United States Patent [19]

Ikeda et al.

[11] Patent Number: 5,575,895

[45] Date of Patent: Nov. 19, 1996

[54] BIOSENSOR AND METHOD FOR PRODUCING THE SAME

[75] Inventors: Shin Ikeda, Katano; Mariko Miyahara, Moriguchi; Toshihiko Yoshioka, Osaka; Shiro Nankai, Hirakata, all of Japan

[73] Assignee: Matsushita Electric Industrial Co., Ltd., Osaka, Japan

[21] Appl. No.: 452,774

[22] Filed: May 30, 1995

[30] Foreign Application Priority Data

Jun. 2, 1994 [JP] Japan .................. 6-120933
Oct. 7, 1994 [JP] Japan .................. 6-244399

[51] Int. Cl.⁶ .................................. G01N 27/26
[52] U.S. Cl. .......... 204/403; 204/412; 204/418; 435/817; 435/287.9; 435/287.1
[58] Field of Search .................... 204/403, 418, 204/412; 435/288, 291, 817

[56] References Cited

U.S. PATENT DOCUMENTS 5,264,103  11/1993  Yoshioka et al. .......... 204/403
5,366,609  11/1994  White et al. ............... 204/403
5,395,504   3/1995  Saurer et al. .............. 204/403

FOREIGN PATENT DOCUMENTS

0359831   3/1990  European Pat. Off. .
2-113316   4/1990  Japan .
6088804   3/1994  Japan .

*Primary Examiner*—Bruce F. Bell
*Attorney, Agent, or Firm*—Panitch Schwarze Jacobs & Nadel, P.C.

[57] ABSTRACT

A biosensor for quantification of a specific component contained in various biological samples comprises an electrically insulating base plate, an electrode system including a working electrode and a counter electrode which are provided on the electrically insulating base plate, a reaction layer formed on the electrode system including at least an oxido-reductase, and an enclosure member having a hollow space constituting a sample supplying channel on the electrically insulating base plate, wherein substantially the whole of the reaction layer is exposed to the hollow space.

20 Claims, 3 Drawing Sheets

BIOSENSOR AND METHOD FOR PRODUCING THE SAME

BACKGROUND OF THE INVENTION

1. Field of the Invention

The present invention relates to a biosensor capable of rapidly quantifying a specific component in a sample, particularly a biological sample, with high accuracy in a simplified manner, and to a method for producing the same.

2. Description of the Prior Art

Heretofore, as a system capable of rapidly quantifying the specific component in a sample solution with high accuracy, there has been known a biosensor (for instance, Japanese Laid-Open Patent Publication No. Hei 3-202,764) which will be described below.

The disclosed conventional biosensor is configured by forming an electrode system composed of a measuring electrode and a counter electrode on an electrically insulating base plate, then forming thereon a reaction layer comprising a hydrophilic polymer, an oxido-reductase and an electron acceptor, and thereafter forming a hollow space constituting a sample supplying channel of the sensor by combining a cover and a spacer with the base plate.

When the sample solution containing a substrate to be quantified is contacted with an inlet of the sample supplying channel, the sample solution is rapidly introduced into the reaction layer due to a capillary phenomenon of the above-mentioned hollow space to dissolve the reaction layer. Then, the substrate is allowed to react with the enzyme contained in the reaction layer and the electron acceptor is reduced. Upon completion of the enzyme reaction, the reduced electron acceptor is electrochemically oxidized to produce an oxidizing current, and based on the value of the oxidizing current obtained with this oxidation reaction, the concentration of the substrate contained in the sample solution can be determined.

Further, the disclosed biosensor is produced by the steps of forming the electrode system on the base plate, forming the reaction layer on the electrode system and combining the cover and the spacer with the base plate, the electrode system and the reaction layer to form the hollow space.

In the configuration of such prior art biosensor, the hollow space formed between the cover and the base plate is tubular-shaped, and therefore the supplied sample solution only contacts a part of the reaction layer that is substantially identical with an outer shape of the electrode system. Therefore, an area occupied by the region of the reaction layer actually dissolved in the sample solution can never be made constant, thereby to create a cause for deteriorating a sensor response-reproducibility of the sensor. Further, according to a production method composed of forming the reaction layer by titrating a solution containing the oxido-reductase on the electrode system and drying the titrated solution, it is difficult to form a homogeneous reaction layer because of overflowing of the solution outside the electrode system.

SUMMARY OF THE INVENTION

The primary object of the present invention is to provide a biosensor that allows rapid and simplified quantification of a specific component contained in various biological samples with high accuracy.

It is another object of the present invention to provide a biosensor having a high sensor response-reproducibility.

It is still another object of the present invention to provide a method for producing such biosensor that can form a homogeneous reaction layer in a simple operation.

The present invention provides a biosensor comprising:
an electrically insulating base plate,
an electrode system including a working electrode and a counter electrode which are provided on a principal face of the electrically insulating base plate,
a reaction layer including at least an oxido-reductase, and
an enclosure member having a hollow space constituting a sample supplying channel on the electrically insulating base plate,
wherein substantially the whole part of the reaction layer is exposed to the hollow space.

The present invention also provides a method for producing a biosensor comprising the steps of:
forming an electrode system including a working electrode and a counter electrode on an electrically insulating base plate,
partitioning the electrically insulating base plate so as to define a section wherein the electrode system is to be exposed by combining an enclosure member with the electrically insulating base plate, and
forming a reaction layer including at least an oxido-reductase in the section defined in the previous step.

The present invention also provides a method for producing a biosensor comprising the steps of:
forming an electrode system including a working electrode and a counter electrode on an electrically insulating base plate,
partitioning the electrically insulating base plate so as to define a section wherein the electrode system is to be exposed by bringing a spacer into close contact with the electrically insulating base plate,
forming a reaction layer including at least an oxido-reductase in the section defined in the previous step, and
bringing a cover into close contact with the spacer.

In the above-mentioned biosensor, the reaction layer preferably comprises an electron acceptor and/or a hydrophilic polymer.

In a preferred embodiment of the present invention, the above-mentioned reaction layer comprises a carrier for carrying at least the oxido-reductase.

Further, the above-mentioned enclosure member preferably comprises a spacer having a slot with an open end which serves as a sample supplying inlet on its tip end and a cover plate laminated with the spacer.

Moreover, a part of the bottom of the hollow space which is on the electrode system is preferably substantially in conformity with an outer shape of the electrode system.

Further, the above-mentioned reaction layer is preferably formed on the electrode system in close contact with the electrode system.

While novel features of the invention are set fourth in the preceding, the invention, both as to organization and content, can be further understood and appreciated, along with other objects and features thereof, from the following detailed description and example when taken in conjunction with the attached drawings.

DETAILED DESCRIPTION OF THE EMBODIMENTS

In the following paragraphs, embodiments of the biosensor and method for producing the same in accordance with the present invention will be described in detail with reference to the attached drawings.

As described above, the biosensor in accordance with the present invention has a configuration wherein substantially the entire reaction layer is exposed to the hollow space, and thus substantially the whole of various components contained in the reaction layer can participate in the reaction. Therefore, the response of the sensor and its reproducibility can remarkably be improved.

Further, according to the above-mentioned production method, it is possible to form a homogeneous reaction layer in a simple operation as follows; first, partitioning the electrically insulating base plate to define the region occupied by the reaction layer by bringing a spacer into close contact with the base plate, and then, forming the reaction layer by titrating a solution for forming the reaction layer to the defined region and drying the titrated solution, or alternatively by placing a carrier carrying various components constituting the reaction layer in the above-mentioned defined region.

As has been described above, according to the present invention, it is possible to improve the response of the reaction layer, because the reaction layer containing various components can be formed homogeneously and part of the reaction layer to be dissolved in the sample solution can be made constant. As a result, a biosensor having a high reproducibility can be obtained.

In the following paragraphs, the present invention will be described in more detail by way of examples with reference to the attached drawings.

Figure 1:
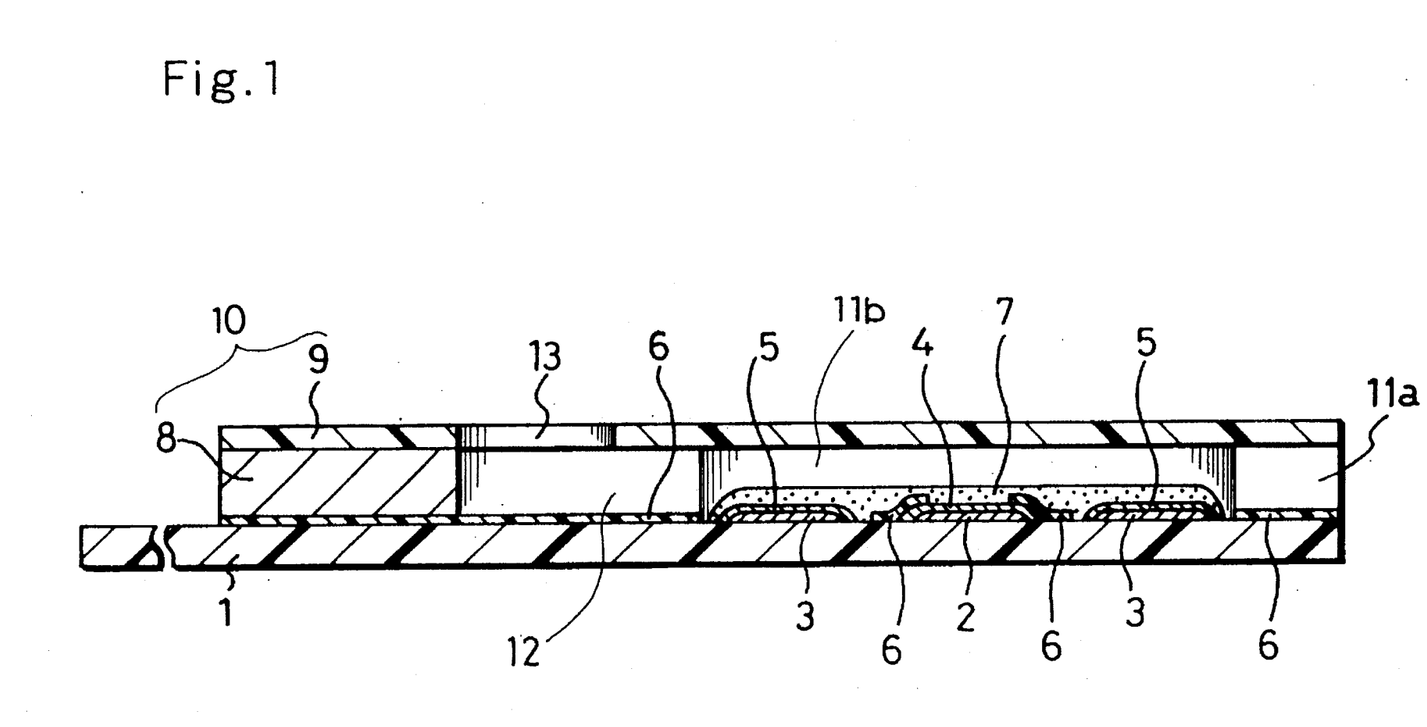
FIG. 1 is a cross-sectional side view showing an essential part of a biosensor prepared in accordance with an embodiment of the present invention.
Figure 2:
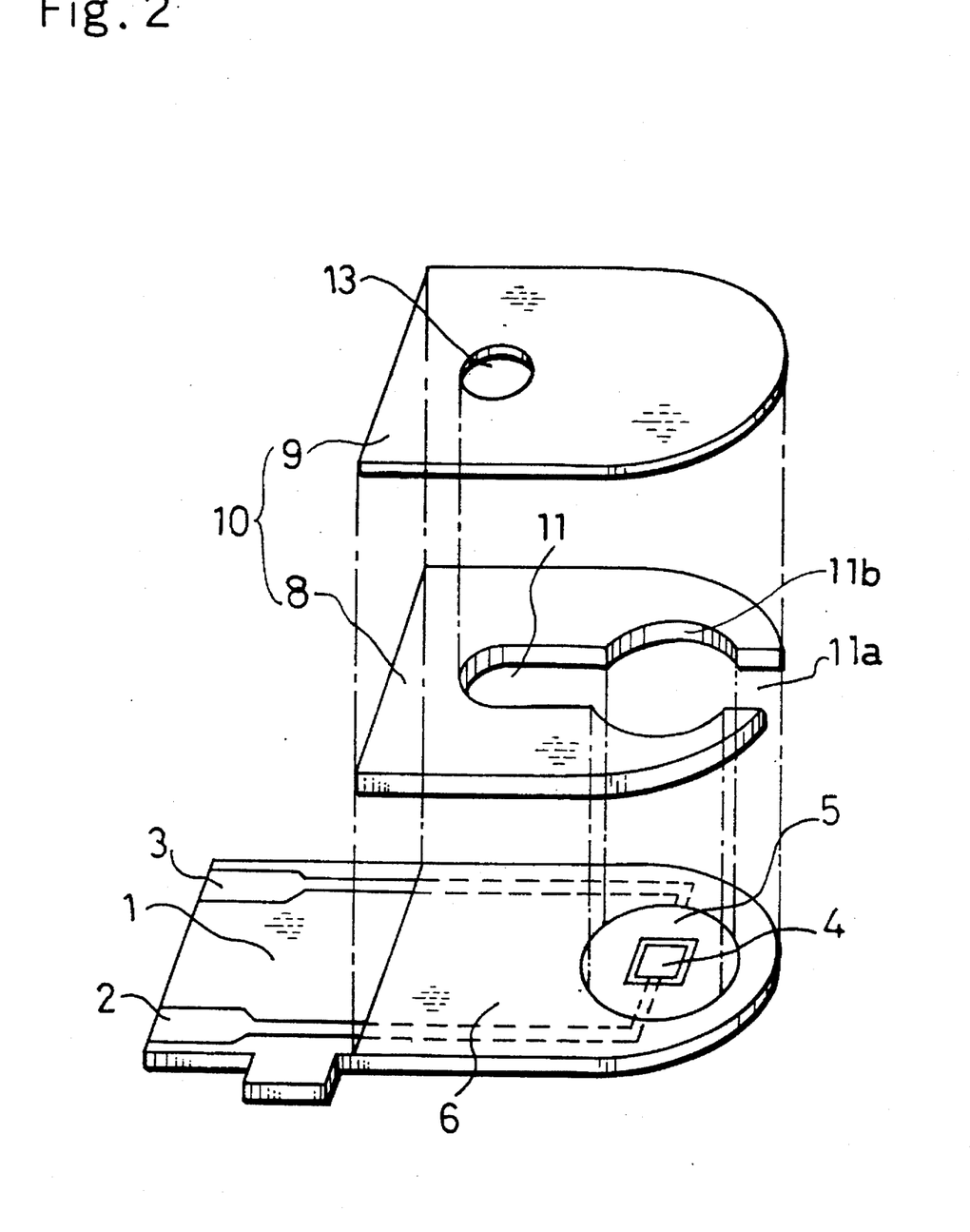
FIG. 2 is an exploded perspective view of the biosensor shown in FIG. 1 excluding the reaction layer, viewed along an oblique-upper direction.

FIG. 1 is a cross-sectional side view showing an essential part of a biosensor in accordance with an embodiment of the present invention, while FIG. 2 is an exploded perspective view of the biosensor shown in FIG. 1 viewed along an oblique-upper direction (wherein its reaction layer is omitted for illustration purpose).

The structure of this biosensor is as follows.

An electrically insulating base plate 1 made of polyethylene terephthalate is provided with a pair of lead conductors 2 and 3 formed by printing a silver paste by a screen printing process. On the base plate 1, there are provided a working electrode 4 and a counter electrode 5, which constitute an electrode system formed by printing using an electrically conductive carbon paste including resin binder. After formation of the lead conductors 2 and 3, an electrically insulating layer 6 is formed using an electrically insulating paste. The electrically insulating layer 6 is provided in order to maintain a constant area (about 1 mm$^2$) of the exposed region of the working electrode 4 and partly cover the lead conductors 2 and 3.

On the electrode system formed on the base plate 1, there is provided a reaction layer 7 which is in close contact with the electrode system. The detailed construction of the reaction layer will be described in the concrete examples below.

An enclosure member 10 comprising a slotted spacer 8 and a cover 9 is adhered to the base plate 1 in a positional relationship as indicated by the single chain lines in FIG. 2. The slotted spacer 8 and the cover 9 define a hollow space on the electrically insulating base plate which constitutes a sample supplying channel 12 which will be described later.

As shown in FIG. 2, the slotted spacer 8 has an elongated slot 11 which includes an approximately rectangular sample supplying inlet 11a at its right end (in the figure) and an arcuate part 11b. The inlet 11a is an open end for the sample supplying channel 12. The arcuate part 11b is provided just over the electrode system and is shaped in conformity with an outer shape of the electrode system. The left or farthest part of the slot 11 lies just under an air vent 13 provided on the cover 9.

Substantially the entire reaction layer 7 is exposed to the hollow space 12 defined by the spacer 8 between the upper face of the base plate 1 and the cover 9. That is, substantially the entire reaction layer 7 is placed in the arcuate part 11b of the rectangular slot 11 including the sample supplying inlet 11a of the sensor. It is therefore preferable that the diameter of the above-mentioned arcuate part 11b is approximately equal to the diameter of the counter electrode 5 and that the reaction layer 7 is formed on the entire region in the arcuate part 11b.

Conventionally, since the slot 11 has been formed straight, the reaction layer 7 is partially covered by the spacer 8. Consequently, it has been impossible to expose the entire surface of the reaction layer 7 to the sample supplying channel 12. If the width of the slot 11 is increased in order to expose the entire surface of the reaction layer 7 to the sample supplying channel 12, the sectional area of the sample supplying channel 12 is increased. As a result, it becomes difficult to introduce a sample solution to the reaction layer 7 only by bringing the sample solution into contact with the open end of the sample supplying channel 12 through the capillary phenomenon of the sample supplying channel 12.

In the below-mentioned embodiments, the width "d" of the slot 11 is 2.0 mm, the diameter of the circular section including the arcuate part 11b is 3.8 mm, and the height "h" of the sample supplying channel 12, that is, the thickness of spacer 8, is 0.4 mm. Preferably, the sample supplying channel 12 should have such sectional area, i.e., d×h, that readily allows introduction of the sample solution to the reaction layer 7 by simply bringing the sample solution into contact with the open end of the sample supplying channel 12.

In order to make the sensor in such a preferable configuration, it is advantageous to form the reaction layer 7 after the spacer 8 is combined with the base plate 1, in the case that the reaction layer is formed by titrating a solution, particularly an aqueous solution containing a hydrophilic polymer, followed by drying the titrated solution. It is also possible to form the reaction layer 7 having a predetermined size at a predetermined position on the base plate and then combine the base plate with the enclosure member, by adequately adjusting the titrating amount and the viscosity of the solution for forming the reaction layer.

Although the enclosure member 10 in the above-mentioned configuration is constituted with two components of the spacer 8 and the cover 9, another configuration may alternatively be adopted such that the enclosure member is formed by molding it in a combination of the spacer 8 with the cover 9 into a unitary body for the sensor configured by employing the latter process of forming the reaction layer. Further, in some instances, the spacer may solely serve as the enclosure member.

EXAMPLE 1

(Fructose Sensor I)

First, an electrically insulating base plate 1 made of polyethylene terephthalate and provided with a pair of lead conductors 2 and 3, an electrode system composed of a working electrode 4 and a counter electrode 5, and an electrically insulating layer 6 was prepared. In this example, an area occupied by the region of the working electrode 4 to be exposed was about 1 $mm^2$.

On the electrode system of the base plate 1, a 0.5 wt % aqueous solution of carboxymethyl cellulose (hereinafter referred to as "CMC") as the hydrophilic polymer was titrated and then dried to form a CMC layer. Subsequently, a reaction layer 7 was formed on the above-mentioned CMC layer by titrating 4 μl of a mixed solution prepared by dissolving 1000 U of fructose dehydrogenase (made by Toyobo; hereinafter referred to as "FDH") as the enzyme and 33 mg of potassium ferricyanide as the electron acceptor in 1 ml of phosphoric acid-citric acid buffer solution (0.2M $Na_2HPO_4$—0.1M $C_3H_4(OH)(COOH)_3$, pH=5.0) containing CMC by 0.5 wt %, and then drying the titrated solution in a warm-air dryer at 50° C. for 10 minutes. In this case, the diameter of the outer periphery of the reaction layer was about 3.6 mm and approximately in conformity with the diameter of the counter electrode.

When the above-mentioned mixture of phosphoric acid, citric acid, FDH and the electron acceptor was titrated on the CMC layer, the first-formed CMC layer was once dissolved and then converted into the reaction layer 7 in a state of being partly mixed with the enzyme and the other components during the subsequent drying process. However, since a completely mixed state was not reached because of no stirring during the process, a state wherein only the CMC directly covered the surface of the electrode system was brought about.

That is, the process effectively prevented possible adsorption of a protein on the surface of the electrode system and possible variation in the characteristics of the electrode system due to a chemical action of such substances having an oxidizing ability as potassium ferricyanide and the like, because the enzyme, electron acceptor and the like were not brought into a direct contact with the surface of the electrode system. As a result, a fructose sensor having a response of high accuracy was obtainable by this process.

Finally, a slotted spacer 8 and a cover 9 were adhered to the base plate 1 in a positional relationship as indicated by the single chain lines in FIG. 2. These spacer 8 and cover 9 for defining a hollow space which constitutes a sample supplying channel which will be described as follows.

When the spacer 8 and cover 9 were mounted on the base plate 1 in the above-mentioned manner, the sample supplying channel was constituted as the hollow space 12 between the base plate 1 and the cover 9 and surrounded by the spacer having the elongated slot 11. By virtue of a capillary phenomenon of this sample supplying channel, the sample solution can easily be introduced into the part of the reaction layer only by simply bringing the sample solution into contact with the sample supplying inlet 11b on the tip end of the sensor. Since the supplying amount of the sample solution depends on the volume of the hollow space defined by the cover and the spacer, preliminarily quantification of the sample solution is unnecessary. Further, since the entire surface of the reaction layer is exposed to the hollow space, the dissolved amount of the reaction layer is made constant and the reproducibility of the sensor response can be improved. Moreover, since evaporation of the sample solution during the measurement can be suppressed to a minimum, it is possible to perform a measurement with high accuracy.

When 3 μl of fructose aqueous solution as the sample solution was supplied through the sample supplying inlet 11a of the fructose sensor produced in the above-mentioned manner, the sample solution rapidly reached a part which was immediately under the air vent 13 of the cover 9 and the reaction layer 7 on the electrode system was dissolved therein.

At a given time after the supply of the sample solution, a pulse voltage of +0.5 V on the basis of the voltage at the counter electrode 5 was applied to the working electrode 4, and the anodic current value 5 seconds after the application was measured. Thereby a response current value, which was proportional to the concentration of fructose contained in the sample solution, was obtained.

When the reaction layer was dissolved in the sample solution, the fructose in the sample solution was oxidized by the FDH to produce 5-keto-fructose. Then, potassium ferricyanide was reduced to potassium ferrocyanide by electrons shifted by the oxidation reaction effected by the FDH. Thereafter, an oxidation current of the resultant potassium ferrocyanide flowed upon application of the above-mentioned pulse voltage. The value of this current corresponded to the concentration of fructose, which is the substrate to be quantified.

EXAMPLE 2

(Fructose Sensor II)

In a manner similar to that in Example 1, a base plate 1 having a printed electrode system was prepared and a spacer 8 was adhered to the base plate in a positional relationship indicated by the single chain lines in FIG. 2.

Subsequently, on the above-mentioned electrode system of the base plate 1, a 0.5 wt % aqueous solution of CMC as the hydrophilic polymer was titrated and then dried to form a CMC layer. Then, a reaction layer 7 was formed on the above-mentioned CMC layer by titrating 4 μl of a mixed solution prepared by dissolving 1000 U of FDH as the enzyme and 33 mg of potassium ferricyanide as the electron acceptor in 1 ml of phosphoric acid-citric acid buffer solution (0.2M $Na_2HPO_4$—0.1M $C_3H_4(OH)(COOH)_3$, pH=5.0) containing CMC by 0.5 wt %, and thereafter drying the titrated solution in a warm-air dryer at 50° C. for 10 minutes. In this case, the diameter of the outer periphery of the reaction layer was about 3.6 mm which was approximately in conformity with the diameter of the counter electrode.

After forming the reaction layer 7 in the above-mentioned manner, a cover 9 was adhered to the spacer 8 in a positional relationship as indicated by the single chain lines in FIG. 2.

Different from the manner in Example 1, the spacer 8 and the cover 9 are adhered separately in this example. Although this makes the manufacturing process of the sensor slightly complicated, it is possible to form a more homogeneous reaction layer 7, because the process ensures maintaining constant expansion of the reaction layer by the spacer 8.

When 3 μl of fructose aqueous solution as the sample solution was supplied through the sample supplying inlet 11a of the fructose sensor produced in the above-mentioned manner, the sample solution rapidly reached a part which was immediately under the air vent 13, and the reaction layer 7 on the electrode system was dissolved therein.

At a given time after the supply of the sample solution, a pulse voltage of +0.5 V on the basis of the voltage at the counter electrode 5 was applied to the working electrode 4, and the anodic current value 5 seconds after the application was measured. Thereby a response current value, which was proportional to the concentration of fructose contained in the sample solution, was obtained.

EXAMPLE 3

(Fructose Sensor III)

Since the sensor of this example is the same as that of Example 2 except for the composition of the reaction layer 7, an illustration will be made here only on the reaction layer 7.

The spacer 8 was adhered to the base plate 1 on which the electrode system had already been printed in a positional relationship as indicated by the single chain lines in FIG. 2 and in a manner similar to that in Example 2. Thereafter, the CMC layer was formed on the above-mentioned electrode system of the base plate 1, by titrating a 0.5 wt % aqueous solution of CMC and then drying the titrated solution. Then, a first layer was formed on the above-mentioned CMC layer by titrating 4 μl of a mixed solution. The mixed solution was prepared by dissolving 1000 U of FDH as the enzyme in 1 ml of phosphoric acid-citric acid buffer solution (0.2M $Na_2HPO_4$—0.1M $C_3H_4(OH)(COOH)_3$, pH=5.0) containing CMC by 0.5 wt %. Then, the titrated solution was dried in a warm-air dryer at 50° C. for 10 minutes. Thereafter, a second layer was formed by titrating 4 μl of 0.5 wt % ethanol solution of polyvinyl pyrrolidone (hereinafter referred to as "PVP") as the hydrophilic polymer, followed by drying the titrated solution at room temperature. Subsequently, a third layer was formed on the above-mentioned second layer by titrating 3 μl of a toluene dispersion, which was prepared by dispersing 190 mg of potassium ferricyanide as the electron acceptor in toluene containing egg-yolk lecithin by 1.0 wt %, followed by drying the titrated dispersion at room temperature.

In this example, the reaction layer 7 is composed of the above-mentioned first, second and third layers. Also in this case, the diameter of the outer periphery of the reaction layer 7 was about 3.6 mm and approximately in conformity with the diameter of the counter electrode.

The sensor of this example has the reaction layer 7 of a laminated structure composed of three layers and its manufacturing process is further complicated than that of Example 2. Since the first layer containing the enzyme is separated from the third layer containing the electron acceptor by the second layer containing the hydrophilic polymer, the enzyme is not in direct contact with the electron acceptor, and therefore, this configuration has an advantage that possible deterioration in the enzyme activity can effectively be prevented during a long-term storing.

When 3 μl of fructose aqueous solution as the sample solution was supplied through the sample supplying inlet 11a of the fructose sensor produced in the above-mentioned manner, the sample solution rapidly reached a part which was immediately under the air vent 13, and the reaction layer 7 on the electrode system was dissolved therein.

At a given time after the supply of the sample solution, a pulse voltage of +0.5 V on the basis of the voltage at the counter electrode 5 was applied to the working electrode 4 and the anodic current value 5 seconds after the application was measured. The measurement gives a response current value which was proportional to the concentration of fructose contained in the sample solution.

EXAMPLE 4

(Glucose Sensor I)

First, an illustration will be made on the preparing process of the glucose sensor. The configuration of the glucose sensor of this example is the same as that in Example 1 except for some components in the reaction layer 7.

On the electrode system of the base plate 1, a 0.5 wt % aqueous solution of CMC was titrated and then dried to form the CMC layer. Subsequently, a reaction layer 7 was formed on the above-mentioned CMC layer by titrating 4 μl of a mixed solution prepared by dissolving glucose oxidase (hereinafter referred to as "GOD") as the enzyme and potassium ferricyanide as the electron acceptor and then drying the titrated solution in a warm-air dryer at 50° C. for 10 minutes. In this case, the diameter of the outer periphery of the reaction layer 7 was about 3.6 mm and approximately in conformity with the diameter of the counter electrode 5.

When the above-mentioned mixture of the GOD and the electron acceptor was titrated on the CMC layer, the first-formed CMC layer was once dissolved and then converted into the reaction layer 7 in a state of being mixed with the enzyme and the other components in the mixture during the subsequent drying process. However, since a completely mixed state was not reached because of no stirring during the process, a state wherein only the CMC layer directly covered the surface of the electrode system was brought about.

Finally, a slotted spacer 8 and a cover 9 were adhered to the base plate 1 in a positional relationship as indicated by the single chain lines in FIG. 2.

When 3 μl of glucose aqueous solution as the sample solution was supplied through the sample supplying inlet 11a of the glucose sensor produced in the above-mentioned manner, the sample solution rapidly reached a part which was immediately under the air vent 13, and the reaction layer 7 on the electrode system was dissolved therein.

At a given time after the supply of the sample solution, a pulse voltage of +0.5 V on the basis of the voltage at the counter electrode 5 was applied to the working electrode 4, and the anodic current value was measured 5 seconds after the application, thereby to obtain a response current value which was proportional to the concentration of glucose contained in the sample solution.

When the reaction layer dissolved in the sample solution, the glucose in the sample solution was oxidized by the GOD to produce gluconolactone. Then, potassium ferricyanide was reduced to potassium ferrocyanide by electrons shifted by the oxidation reaction effected by the GOD. Thereafter, an oxidation current of the resultant potassium ferrocyanide flowed upon application of the above-mentioned pulse voltage. The value of this current corresponded to the concentration of glucose, which is the substrate to be quantified.

The glucose sensor wherein substantially the entire reaction layer is exposed to the hollow space defined by the spacer and the cover as in this example is named "A". A glucose sensor of the prior art having a tubular-shaped hollow space, namely a glucose sensor having a slot as shown in FIG. 2 wherein the sample supplying channel 11 lacks the arcuate part 11b, is named "B". Variances in the responses obtained with these sensors are compared in terms of the coefficient of variance and the results are summarized in Table 1 below. The relationship between the glucose concentration and the response current is illustrated in FIG. 3.

Figure 3:
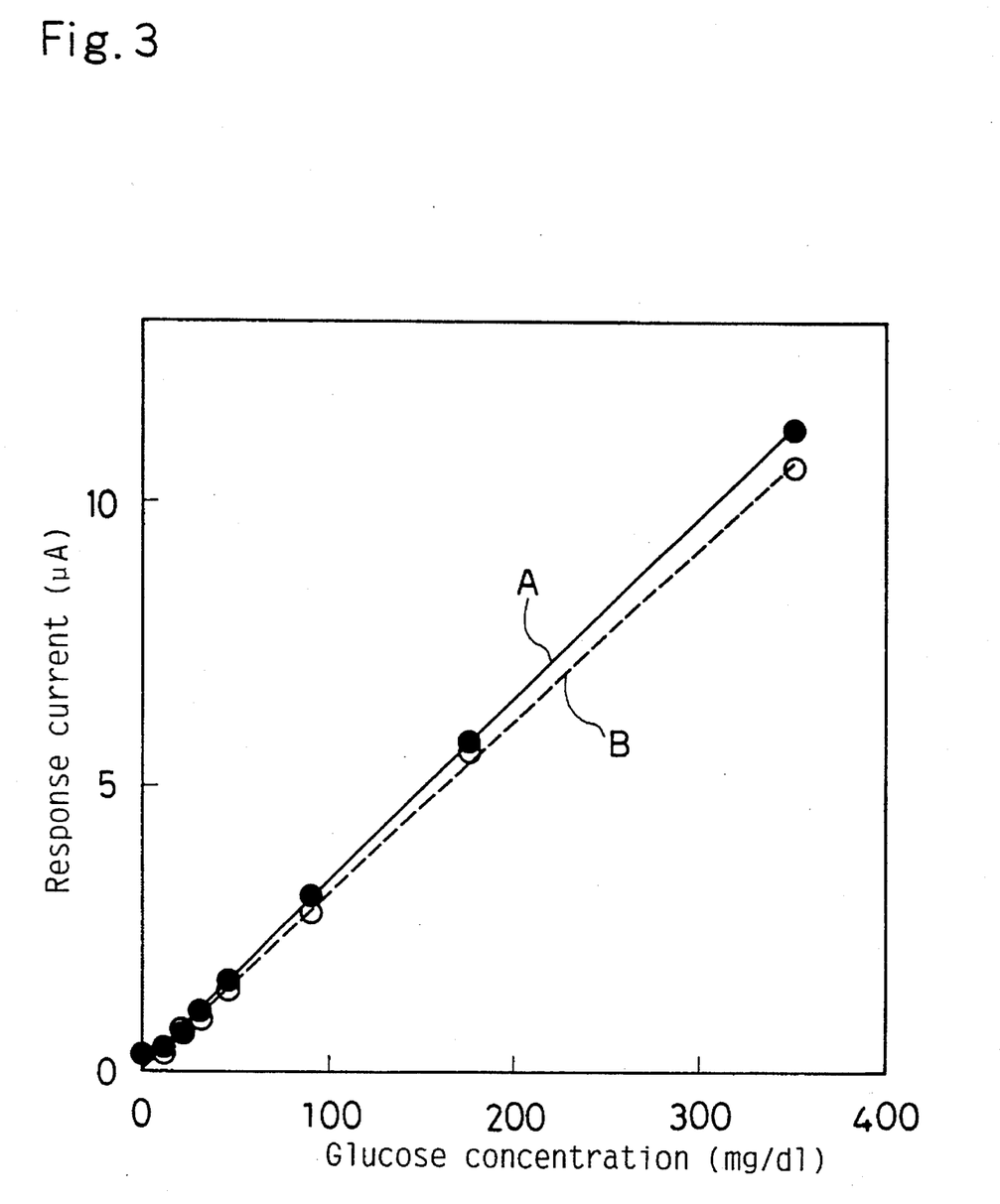
FIG. 3 is a graph showing the relationship between the glucose concentration and the response current of the glucose sensor in the example of the present invention and the comparative example.

As shown in Table 1 and FIG. 3, it is clearly understood that the glucose sensor "A", in which the response current of the sensor increases in correspondence with a decrease in the coefficient of variance at a glucose concentration of greater than 30 mg/dl, is superior to the glucose sensor "B".

TABLE 1

| Concentration of glucose (mg/dl) | A Response value (µA) Coefficient of variance | B Response value (µA) Coefficient of variance |
| --- | --- | --- |
| 0 | 0.3 | 0.3 |
|  | 9.1 | 13.0 |
| 11 | 0.4 | 0.3 |
|  | 19.2 | 8.9 |
| 21 | 0.7 | 0.7 |
|  | 3.2 | 7.6 |
| 30 | 1.1 | 1.0 |
|  | 4.6 | 5.2 |
| 45 | 1.6 | 1.4 |
|  | 3.1 | 3.1 |
| 90 | 3.1 | 2.8 |
|  | 2.3 | 3.4 |
| 176 | 5.9 | 5.7 |
|  | 1.3 | 1.9 |
| 353 | 11.4 | 10.1 |
|  | 0.9 | 1.4 |

EXAMPLE 5

(Glucose Sensor II)

Since the sensor of this example is the same as that of Example 4 except for the composition of the reaction layer 7, an illustration will be made here only on the reaction layer 7.

The spacer 8 was bonded to the base plate 1 on which the electrode system had already been printed in a positional relationship as indicated by the single chain lines in FIG. 2 in a manner similar to that in Example 4. Thereafter, a piece of filter paper impregnated with GOD as the enzyme and potassium ferricyanide as the electron acceptor was placed on the above-mentioned electrode system. And then the cover 9 was adhered to the spacer 8 in the positional relationship as indicated by the single chain lines in FIG. 2 to complete the glucose sensor. In this case, the diameter of the outer periphery of the reaction layer 7 was about 3.6 mm and approximately in conformity with the diameter of the counter electrode 5.

Glucose aqueous solution of 3 µl as the sample solution was supplied through the sample supplying inlet 11a of the glucose sensor produced in the above-mentioned manner. Then, the sample solution rapidly reached a part corresponding to the air vent 13, and the enzyme and the electron acceptor in the reaction layer 7 on the electrode system were dissolved therein.

At a given time after the supply of the sample solution, a pulse voltage of +0.5 V on the basis of the voltage at the counter electrode 5 was applied to the working electrode 4, and the anodic current value 5 seconds after the application of the pulse voltage was measured. The measurement gives a response current value which was proportional to the concentration of glucose contained in the sample solution.

In Examples 4 and 5 just described above, the illustration has been made on the biosensors which employ the electron acceptor in the reaction layer, but it is also possible to configure a biosensor which does not employ the electron acceptor. That is, a technical advantage similar to those in the above-mentioned examples is obtained with a biosensor; wherein the electrode system is configured with platinum, gold or the like, and the reaction layer containing only the enzyme, or that containing the enzyme and the hydrophilic polymer is formed on the electrode system. In such a biosensor, the substrate concentration is determined based on the concentration of hydrogen peroxide produced as a result of the enzyme reaction, or the concentration of oxygen consumed by the enzyme reaction.

In the above-mentioned examples, although the reaction layer is placed in close contact with the electrode system, the present invention is not limited to the biosensors configured by placing the reaction layer in close contact with the electrode system but may alternatively be embodied in a biosensor which has a configuration wherein a clearance is placed between the electrode system and the reaction layer, or between the cover and the reaction layer.

Further, although the reaction layer is entirely formed on the electrode system in the above-mentioned examples, the present invention is not limited to this configuration, but may employ another configuration wherein the reaction layer is formed in the hollow space defined by the enclosure member and substantially the entire reaction layer is exposed to the hollow space, but in a state that the reaction layer is not in conformity with the electrode system.

In addition, although the bottom face of the above-mentioned hollow space on the region of the electrode system is substantially in conformity with the outer shape of the electrode system in the above-mentioned examples, the present invention is not limited to this, but may be embodied in a configuration; wherein substantially the entire reaction layer is exposed to the hollow space, even in such case that the bottom face of the above-mentioned hollow space on the region of the electrode system is not substantially in conformity with the outer shape of the electrode system.

In the above-mentioned examples, although fructose dehydrogenase (FDH) or glucose oxidase (GOD) is used as the oxido-reductase, the present invention is not necessarily limited to these enzymes. Alternatively, an excellent response of the sensor can be obtained by using an enzyme system produced by combining hexokinase, phosphoglucose isomerase and glucose-6-phosphate dehydrogenase, or another enzyme system produced by combining glucose isomerase with glucose oxidase in place of the above-mentioned FDH.

In addition, a technical advantage similar to that of the fructose sensor described in the examples may be obtained with sensors such as lactic acid sensor which employs lactic acid oxidase or lactic acid dehydrogenase as the enzyme, glucose sensor which employs glucose dehydrogenase, cholesterol sensor which employs cholesterol oxidase or cholesterol dehydrogenase, urea sensor which employs urease, or sucrose sensor which employs an enzyme system of a combination of glucose oxidase and invertase or a combination of fructose dehydrogenase, invertase and mutarotase.

Further, although carboxymethyl cellulose and/or polyvinyl pyrrolidone are used as the hydrophilic polymer in the above-mentioned examples, the present invention is not limited to this configuration. A technical advantage similar to these may alternatively be obtained by employing any of polyvinyl alcohol, gelatin and its derivatives, acrylic acid and its salts, methacrylic acid and its salts, starch and its derivatives, maleic anhydride and its salts, and a cellulose derivative, more concretely, hydroxypropyl cellulose, methyl cellulose, ethyl cellulose, hydroxyethyl cellulose, ethylhydroxyethyl cellulose and carboxymethylethyl cellulose.

On the other hand, although potassium ferricyanide shown in the above-mentioned examples is excellent as the electron acceptor in view of its stability and its reaction rate, p-benzoquinone or ferrocene may be employed, alternatively.

In addition, although filter paper is used as the carrier which constitutes the reaction layer in the above-mentioned examples, the present invention is not limited to this, and alternatively, an insoluble polymer such as nitrocellulose or cellulose triacetate may be employed. Further, the above-mentioned hydrophilic polymer may also be used as the carrier. In this case, a dried substance of a solution of the hydrophilic polymer which dissolves at least an enzyme may be used as the reaction layer.

In the foregoing embodiments, although the two-electrode system comprising the working electrode and the counter electrode is illustrated, it is also possible to perform a measurement with higher accuracy by employing a three-electrode system which further comprises a reference electrode in addition to the working electrode and the counter electrode.

As has been clarified in the above description, according to the present invention, a biosensor having a high reliability can be produced because the sensor thus obtained has a homogeneous reaction layer the entirety of which uniformly participates in the reaction.

It is understood that various other modifications will be apparent to and can be readily made by those skilled in the art to which this invention pertains without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof, by those skilled in the art to which this invention pertains.

What is claimed is:

1. A biosensor comprising:
   an electrically insulating base plate,
   an electrode system including a working electrode and a counter electrode which are provided on a principal face of said electrically insulating base plate,
   a reaction layer including at least an oxido-reductase, and
   an enclosure member having a hollow space constituting a sample supplying channel having a width which is less than the width of said electrode system on said electrically insulating base plate,
   wherein substantially the entire electrode system is located on the bottom of said hollow space and substantially the entire reaction layer is exposed to said hollow space.

2. The biosensor in accordance with claim 1, wherein said reaction layer comprises an electron acceptor.

3. The biosensor in accordance with claim 1, wherein said reaction layer further comprises a hydrophilic polymer.

4. The biosensor in accordance with claim 1, wherein said enclosure member comprises a spacer having a slot with an open end which serves as a sample supplying inlet on its tip end and a cover plate laminated with said spacer.

5. The biosensor in accordance with claim 4, wherein said spacer has an arcuate part which is provided over said electrode system and is shaped in conformity with an outer shape of said electrode system.

6. The biosensor in accordance with claim 1, wherein a part of the bottom of said hollow space which is on said electrode system is substantially in conformity with an outer shape of said electrode system.

7. The biosensor in accordance with claim 1, wherein said reaction layer comprises a carrier for carrying at least said oxido-reductase.

8. The biosensor in accordance with claim 1, wherein said reaction layer is formed on said electrode system in contact with said electrode system.

9. A method for producing a biosensor comprising the steps of:
   forming an electrode system including a working electrode and a counter electrode on an electrically insulating base plate,
   partitioning said electrically insulating base plate to define a section wherein substantially the entire electrode system is to be exposed by combining an enclosure member with said electrically insulating base plate, and
   forming a reaction layer including at least an oxido-reductase only in said section defined in the previous step.

10. The method for producing a biosensor in accordance with claim 9, wherein said step of forming said reaction layer comprises forming a reaction layer including a hydrophilic polymer and an oxido-reductase.

11. The method for producing a biosensor in accordance with claim 9, wherein said step of forming said reaction layer comprises forming a reaction layer including an oxido-reductase and an electron acceptor.

12. The method for producing a biosensor in accordance with claim 9, wherein said step of forming said reaction layer comprises forming a reaction layer including a hydrophilic polymer, an oxido-reductase and an electron acceptor.

13. The method for producing a biosensor in accordance with claim 9 wherein the enclosure member includes a spacer, the partitioning step further including combining the spacer with the base plate, wherein the reaction layer forming step occurs after the combining step.

14. A method for producing a biosensor comprising the steps of:
   forming an electrode system including a working electrode and a counter electrode on an electrically insulating base plate,
   partitioning said electrically insulating base plate to define a section wherein substantially the entire electrode system is to be exposed by bringing a spacer into contact with said electrically insulating base plate,
   forming a reaction layer including at least an oxido-reductase only in said section defined in the previous step, and
   bringing a cover into contact with said spacer.

15. The method for producing a biosensor in accordance with claim 14, wherein said spacer has a slot with an open end which serves as a sample supplying inlet on its tip end.

16. The method for producing a biosensor in accordance with claim 15, wherein said spacer has an arcuate part which is provided over said electrode system and is shaped in conformity with an outer shape of said electrode system.

17. The method for producing a biosensor in accordance with claim 14 wherein the partitioning step further includes combining the spacer with the base plate, wherein the reaction layer forming step occurs after the combining step.

18. A method for producing a biosensor comprising the steps of:

forming an electrode system including a working electrode and a counter electrode on an electrically insulating base plate, partitioning said electrically insulating base plate to define a section wherein substantially the entire electrode system is to be exposed by bringing a spacer into contact with said electrically insulating base plate, forming a reaction layer comprising a carrier carrying at least an oxido-reductase only in said section defined in the previous step, and bringing a cover into contact with said spacer.

19. The method for producing a biosensor in accordance with claim 18, wherein said carrier carries an electron acceptor.

20. The method for producing a biosensor in accordance with claim 18 wherein the partitioning step further includes combining the spacer with the base plate, wherein the reaction layer forming step occurs after the combining step.

* * * * *